United States Patent
Botten

(10) Patent No.: US 11,911,309 B2
(45) Date of Patent: Feb. 27, 2024

(54) OSTOMY POUCH CLOSURE SYSTEM

(71) Applicant: Hollister Incorporated, Libertyville, IL (US)

(72) Inventor: Ronald S. Botten, Libertyville, IL (US)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 18/547,540

(22) PCT Filed: Dec. 22, 2022

(86) PCT No.: PCT/US2022/053774
§ 371 (c)(1),
(2) Date: Aug. 23, 2023

(87) PCT Pub. No.: WO2023/129465
PCT Pub. Date: Jul. 6, 2023

(65) Prior Publication Data
US 2024/0033118 A1    Feb. 1, 2024

Related U.S. Application Data

(60) Provisional application No. 63/294,459, filed on Dec. 29, 2021.

(51) Int. Cl.
*A61F 5/44* (2006.01)
*A61F 5/445* (2006.01)

(52) U.S. Cl.
CPC ............ *A61F 5/4407* (2013.01); *A61F 5/445* (2013.01)

(58) Field of Classification Search
CPC ...... A61F 5/4407; A61F 5/445; A61F 5/4405; A61F 5/443; A61F 5/448; A61F 5/4404; A61F 5/449; A61F 2005/4483; A61F 13/5616; A61F 5/441; A61F 5/442; A61F 5/44; A61L 28/00; B65D 33/24; B65D 35/44; Y10T 24/15; A61B 5/6811; B32B 2535/00

See application file for complete search history.

(56) References Cited

U.S. PATENT DOCUMENTS

| 5,968,024 | A  | 10/1999 | Freeman |
| 6,858,023 | B2 | 2/2005  | Poulsen |

(Continued)

FOREIGN PATENT DOCUMENTS

| WO | 2018187427 A1 | 10/2018 |
| WO | 2020226861 A1 | 11/2020 |

OTHER PUBLICATIONS

International Search Report issued by ISA/EPO in connection with PCT/US2022/053774 dated Mar. 31, 2023.

(Continued)

*Primary Examiner* — Nicholas J. Weiss
*Assistant Examiner* — Brandon W. Levy
(74) *Attorney, Agent, or Firm* — Levenfeld Pearlstein, LLC

(57) ABSTRACT

A closure system for a drainable ostomy appliance, which appliance includes a body side wall and a non-body side wall sealed to one another to define a collection cavity and a neck portion terminating in a discharge outlet. The closure system includes a first portion on the body side wall having first and second closure members defining a gap therebetween and a second portion on the non-body side wall having a third closure member having an enlarged head portion. In an open state, the neck portion is unfolded. In a closed state, the first closure member is folded onto the third closure member with an edge of the first member engaging the enlarged head through the side wall sheet material, and the first, second and third closure members folded over onto the non-body side wall at a tight fold to seal the discharge outlet.

18 Claims, 4 Drawing Sheets

(56) References Cited

U.S. PATENT DOCUMENTS

| | | |
|---|---|---|
| 7,879,016 B2 | 2/2011 | Mandzij et al. |
| 8,500,707 B2 | 8/2013 | Murray |
| 9,011,395 B2 | 4/2015 | Friske et al. |
| 9,629,744 B2 | 4/2017 | Villefrance et al. |
| 2002/0010444 A1 | 1/2002 | Wiltshire et al. |
| 2003/0028160 A1* | 2/2003 | Leise, Jr. ............... A61F 5/4407 604/334 |
| 2003/0167042 A1* | 9/2003 | Poulsen ................. A61F 5/443 604/327 |
| 2005/0159717 A1 | 7/2005 | Holtermann |
| 2008/0033379 A1 | 2/2008 | Pedersen |
| 2008/0051743 A1* | 2/2008 | Falconer ............... A61F 5/4407 604/277 |
| 2012/0022477 A1 | 1/2012 | Grum-Schwensen |
| 2019/0328572 A1 | 10/2019 | Weinberg et al. |

OTHER PUBLICATIONS

Written Opinion issued by ISA/EPO in connection with PCT/US2022/053774 dated Mar. 31, 2023.
International Search Report issued by ISA/EPO in connection with PCT/US2022/053767 dated Mar. 31, 2023.
Written Opinion issued by ISA/EPO in connection with PCT/US2022/053767 dated Mar. 31, 2023.

\* cited by examiner

OSTOMY POUCH CLOSURE SYSTEM

This is a National Stage Application of International Patent Application No. PCT/US2022/053774, filed Dec. 22, 2022, which claims the benefit of and priority to U.S. Provisional Application No. 63/294,459, filed Dec. 29, 2021, the entireties of which are incorporated fully herein by references.

BACKGROUND

The following description relates generally to an ostomy pouch closure system and more particularly to a drainable ostomy pouch closure system.

Ostomy pouches for collecting body waste are used by patients who have had surgery such as a colostomy, ileostomy, or urostomy. Ostomy pouches typically include flat, opposing side walls secured to one another along their peripheral edges to define a collection cavity. An opening for receiving a stoma is formed in one of the side walls, and includes a securing means or system, such as an adhesive barrier, to secure the pouch to the user so that body waste discharged through the stoma is received within the cavity.

Some ostomy pouches may be closed-end pouches designed for single use, in which the entirety of the peripheral edges are sealed to one another and the pouch is discarded after it has been substantially filled with stomal discharge. Other ostomy pouches are drainable pouches that include a discharge opening at a lower end that can be closed during collection of body waste material but may be opened for draining body waste material from the pouch after a period of use. Such drainable pouches are disclosed, for example, in Nolan, U.S. Pat. No. 3,523,534, and Jensen et al., U.S. Pat. No. 4,411,659, which are incorporated herein in their entirety by reference.

The discharge opening of drainable pouches is typically formed at the end of a narrowed neck portion. The end of the neck portion has closure means (or a closure system) for maintaining the discharge opening in a sealed state until waste material is to be drained from the pouch. Some closure systems include a clamp, as in the aforementioned Nolan patent, or a device such as a conventional wire tie or wrap for securing the neck portion in an upwardly-rolled condition.

Drainable pouches should be easy to drain without the risk of soiling one's clothes or the surroundings. Pouches should also be easy to close securely after being drained and amenable to being cleaned after drainage and before re-closing, so that the risk of an unpleasant odor is substantially reduced. Most importantly, the closure system should provide a secure seal when closed to minimize the risk of leakage.

A number of different closure system solutions that facilitate closing, cleaning and drainage operations are known. For example, systems that include upwardly folding portions of the neck with a number of integral spring-like biasing members include Villefrance et al., U.S. Pat. No. 7,879,015 and Friske et al., U.S. Pat. No. 8,672,907, which are commonly assigned with the present application and incorporated herein in their entirety by reference.

Other drainable pouches having integral closure systems include Friske et al., U.S. Pat. No. 9,011,395, which includes four closure members and a two-part fastening system, in which one closure member is provided on a body-side pouch outlet and three closure members are provided on a distal-side pouch outlet, which patent is commonly assigned with the present application and incorporated herein in its entirety by reference.

While all of these system function well, there are critical tolerances for positioning of the stiffening ribs that must be met in order for the closure systems to function properly.

Accordingly, it is desirable to provide an ostomy appliance, such as an ostomy pouch, with a closure system that uses stiffening ribs to effect proper closure. Desirably, in such a system the location and positioning of the closure members or stiffening ribs relative to one another is less critical than in known closure systems. More desirably still, such a system provides a secure closure system that allows for easily opening and emptying of the pouch.

SUMMARY

According to one embodiment, a drainable ostomy appliance includes side walls of flexible sheet material sealed to one another along a portion of their respective peripheries to define a collection cavity. The side walls are a body side wall and a non-body side wall. An inlet is formed in the body side wall.

The side walls define a downwardly extending neck portion terminating in a discharge outlet at which the side walls are not sealed to one another. The discharge outlet is closed by folding the neck portion upwardly and opened by unfolding the neck portion downwardly for draining the contents from the cavity.

The closure system includes a first portion on the body side wall, a second portion on the non-body side wall, and a fastening system. The first portion comprises at least one body side closure member and the second portion of the closure system comprises at least one non-body side closure member including an enlarged head portion on an end thereof.

In an open state, the neck portion is unfolded. In a closed state, the neck portion is folded upwardly at least two times and secured in the closed state using the fastening system, wherein the side walls of the neck portion are folded around the enlarged head portion of the at least one non-body side closure member at a first fold.

In an embodiment, the at least one body side closure member includes a first closure member and a second closure member. The first closure member is proximal the discharge outlet and the second closure member is distal of the discharge outlet. The first and second closure members define a gap therebetween. The at least one non-body side closure member includes a third closure member having the enlarged head portion forming a wipe seal on an end thereof proximal the discharge outlet. In such an embodiment, the first closure member is folded onto the third closure member with an edge of the first member engaging the enlarged head portion through the side walls, and the first, second and third closure members are folded over onto the non-body side wall at a tight fold to seal the discharge outlet. The first and second closure members may have preferential fold lines formed therein. The fold lines can be formed as slits formed into a portion of the first and second closure members. In an embodiment, the third closure member may be formed from a material that is softer than a material from which the first and/or second closure members are formed.

In another embodiment, the at least one non-body side closure member includes a third closure member arranged proximal the discharge outlet and having the enlarged head portion on an end thereof distal of the discharge outlet. The at least one body side closure member includes a first closure member arranged spaced away from the discharge outlet. In the closed state of such an embodiment, the third closure member is folded onto the first closure member at the first fold, and the first and third closure members are folded over onto the non-body side wall at a second fold.

In embodiments, each of the at least one body side closure member and the at least one non-body side closure member may be formed from a stiff, flexible, spring-like material. The material can be, for example, a polymeric material, such as polyethylene (PE) or ethylene vinyl acetate (EVA).

The enlarged head portion can be formed having a variety of shapes, such as a rounded arrowhead shape, an inverted, rounded arrowhead shape, a semicircular projection extending from a side of the third closure member, and the like.

In embodiments, each of the at least one body side closure member is mounted to the body side wall such that a portion of each of the at least one body side closure member is adhered to the body side wall and another portion of each of the at least one body side closure member is not adhered to the body side wall. Likewise, each of the at least one non-body side closure member can be mounted to the non-body side wall such that a portion of each of the at least one non-body side closure member is adhered to the non-body side wall and another portion of each of the at least one non-body side closure member is not adhered to the non-body side wall.

In embodiments wherein the at least one body side closure member includes first and second closure members, the portion of each of the first and second closure members not adhered to the body side wall are proximal one another. And, in embodiments wherein the at least one non-body side closure member includes a third closure member, the portion of the third closure member not adhered to the non-body side wall is proximal the enlarged head portion.

The ostomy appliance can include a two-piece coupling for securing to a user's body.

Other objects, features, and advantages of the disclosure will be apparent from the following description, taken in conjunction with the accompanying sheets of drawings, wherein like numerals refer to like parts, elements, components, steps, and processes.

BRIEF DESCRIPTION OF THE DRAWINGS

FIGS. 4A-4C are sectional views of the pouch illustrating the folding of the closure system, in which FIG. 4A illustrates the pouch in an open or unfolded state, FIG. 4B illustrates a first fold of the closure system, and FIG. 4C illustrates a second or final fold of the closure system to a closed state;

DETAILED DESCRIPTION

Figure 1:
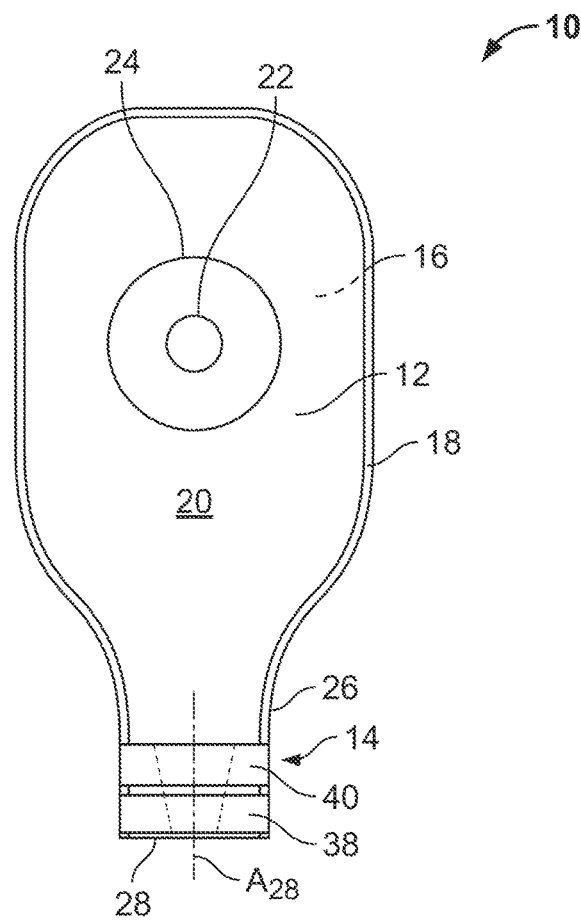
FIG. 1 is a body side view of an ostomy pouch having an embodiment of a closure system in accordance with the present disclosure.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

FIG. 1 illustrates a drainable ostomy appliance or pouch 10, showing the body facing side 12 and shows an ostomy pouch closure system 14, according to an embodiment. The drainable pouch includes an outer wall (or non-body side wall) 16 and the body side wall 12, which are joined along their peripheral edges 18 to define a collection cavity 20 for collecting stomal discharge. The pouch 10 includes an opening 22 for receiving a stoma and a member 24 for securing the pouch 10 to a user, which member 24 surrounds the opening 22. The securing member 24 can be, for example, a one-piece barrier or a two-piece barrier that includes mating coupling rings (not shown). The one- and two-piece barriers will be appreciated by those skilled in the art.

The drainable pouch 10 also has a downwardly extending neck portion 26 terminating in a discharge opening or outlet 28 for draining the contents collected in the cavity 20 after a period of use. The discharge outlet 28 is closed during use by folding the neck portion 26 upwardly and securing it in the upwardly folded position.

The side walls 12, 16 are formed of a suitable flexible sheet material, such as a polymeric film, which can be a monolayer or multilayer film. Each of the walls 12, 16 can be formed of one continuous flexible film to define the entire pouch 10 including the neck portion 26. Alternatively, the walls 12, 16 of the neck portion 26 can be formed of separate flexible films than the walls 12, 16 of the pouch 10 body. That is, the walls of the neck portion 26 may be formed of a different polymeric film than the walls of the pouch body.

Figure 2:
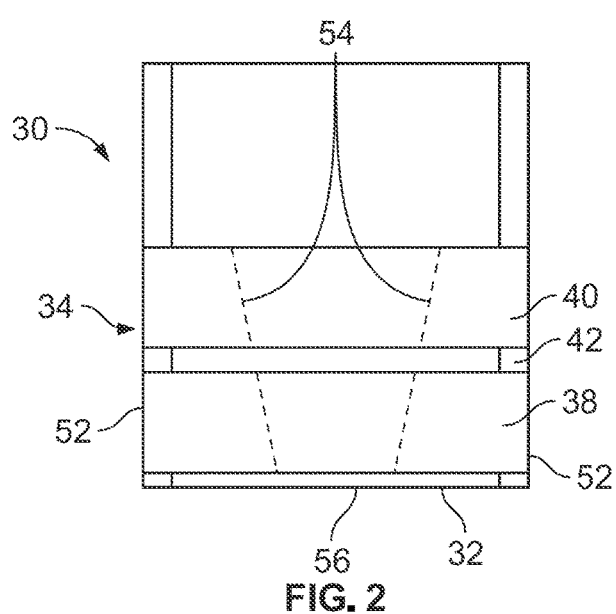
FIG. 2 is a body side view of the lower portion of the pouch illustrating portions of the closure system, according to an embodiment.

Referring now to FIG. 2 there is shown a body side view of a lower portion 30 of the pouch 10. The peripheral edges 18 of the walls 12, 16 are sealed along their respective sides but are not sealed at the bottom, as indicated at 32, which non-sealed region defines the discharge outlet 28 through which stomal discharge can be emptied from the pouch 10.

The closure system 14 includes a first portion 34 on the body side wall 12 and a second portion 36 on the non-body side wall 16. First and second body side closure members 38, 40 are positioned on the body side wall 12, with the body side first closure member 38 proximal to the discharge outlet 28 and the second closure member 40 distal from the discharge outlet 28. A gap 42 is defined between the first and second body side closure members 38, 40.

Figure 3:
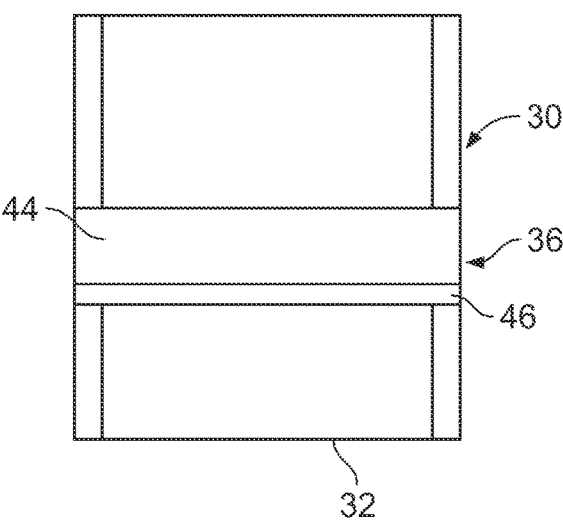
FIG. 3 is a non-body side view of a lower portion of the pouch illustrating portions of the closure system, according to an embodiment.

Referring now to FIG. 3, there is shown a non-body side wall 16 view of the lower portion 30 of the pouch 10. The non-body side wall 16 includes a closure member 44, referred to as the third closure member. The non-body side (third) closure member 44 overlies, at least in part, the body side second closure member 40. In embodiments the third (non-body side) closure member 44 includes a wiper seal 46 which, as illustrated, is formed as an enlarged head portion 48, such as the rounded arrowhead shaped wiper 50 illustrated in FIGS. 4A-4C and 6A. The enlarged head portion 48 is at the downstream (i.e., toward or proximal the outlet 28)

side of the third closure member 44, and aligns with the gap 42 between the first and second closure members 38, 40.

In an embodiment, the closure members 38, 40, 44 are formed from a stiff but flexible, spring-like polymeric material. The members 38, 40, 44 are normally flat and disposed in straight parallel relation to each other. The material is somewhat rigid, but can be bent or flexed to open the discharge opening 28. That is, when in a relaxed state, the closure members 38, 40, 44 maintain the opening 28 in a relatively closed state. But, when the ends 52 of the members 38, 40, 44 are squeezed together (squeezed toward a centerline $A_{28}$ of the discharge opening 28), the members 38, 40, 44 flex or bow outward so as to open the discharge opening 28. Suitable materials for the closure members 38, 40, 44 include polyethylene (PE), ethylene vinyl acetate (EVA) and the like. Closure member 44 may be formed of a material that is softer than the material from which members 38 and 40 are formed. Other materials will be recognized by those skilled in the art.

To facilitate the flexing or bowing outward, in embodiments, the first and second closure members 38, 40 can include preferential fold lines 54. The preferential fold lines 54 can be formed as partial slits in the members 38, 40; the slits are partial in that they do not extend fully through the members 38, 40. As seen in FIG. 2, the fold lines 54 in the first body side member 38, which member 38 is closer to outlet 28 are closer to one another than the fold 54 lines in the second body side member 40. In this manner, when the ends 52 of the members 38/40, 44 are squeezed toward one another to open the discharge opening 28, the closure members 38, 40 will bend or flex to form a funnel-like discharge 56 along the lines 54 for the emptying pouch 10.

Figure 4A:
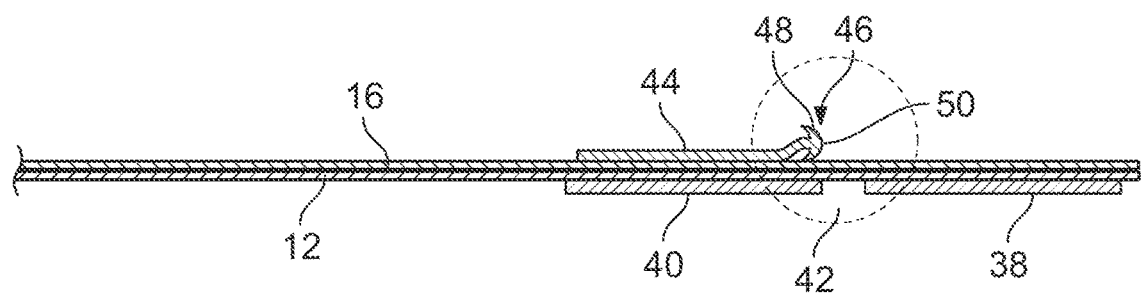
Figure 4B:
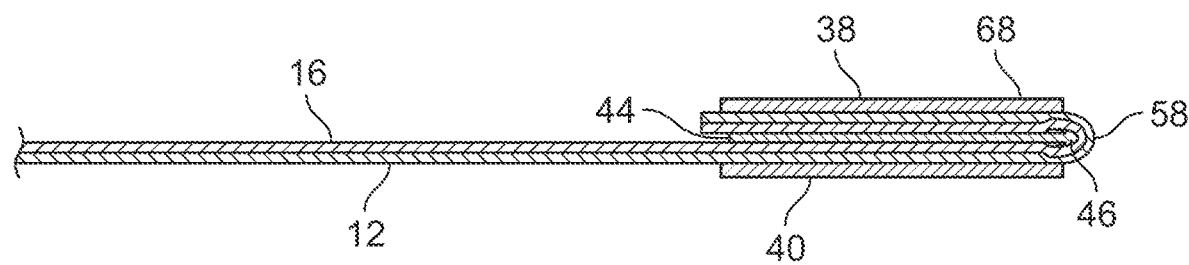
Figure 4C:
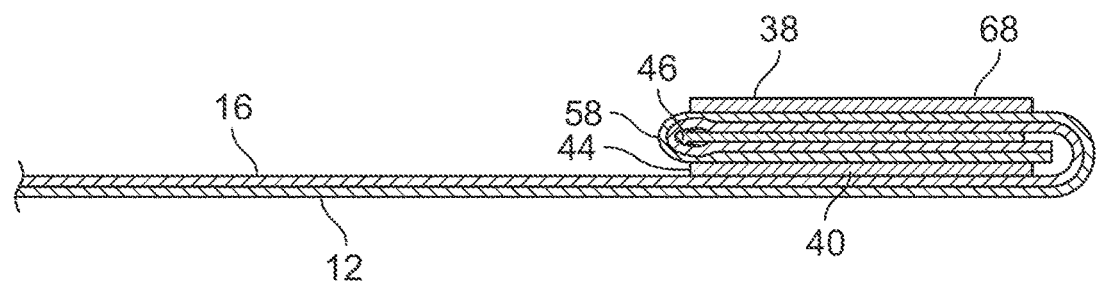

Referring now to FIGS. 4A-4C, the folding of the pouch neck portion 26 to close the pouch discharge opening 28 will be discussed. FIG. 4A shows the pouch 10 with the outlet 28 flat. As noted above, the body side closure members 38, 40 are spaced from one another by the gap 42 and the non-body side closure member 44 overlies, at least in part, the body side second closure member 40, with the enlarged head portion 48 aligned with or overlying the gap 42.

Referring to FIG. 4B, as the first fold (indicated at 58) is made, the first closure member 38 is folded onto the third closure member 44. The pouch material in the space or gap 42 between the first and second members 38, 40 is configured to overlie and compress the wiper seal 46, but allow the wiper seal 46 to lie flat or not fold over onto itself. An inner edge 68 of the first closure member 38 engages the enlarged head portion 48 through the pouch or side wall 14, 16 material, such that the (outlet) fold 58 creates a tension in the pouch 10 material at the fold 58.

Referring now to FIG. 4C, as the second fold (indicated at 60) is made, the first, second, and third members 38, 40, 44 are folded onto the non-body side wall 16. The tight fold as at 60 and stretch of the pouch 10 material at the fold 60 between the second and third members 40, 44 helps to establish a seal of the pouch outlet 28.

Figure 5:
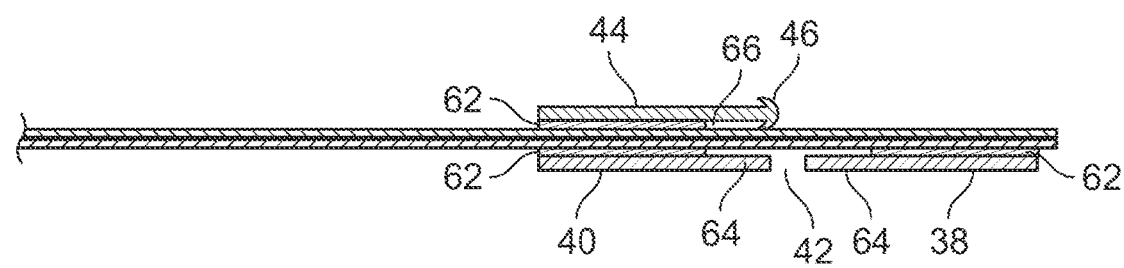
FIG. 5 is a sectional view of the of the pouch illustrating an embodiment of the closure system and showing the anchor points of the stiffening members to the pouch films.

In embodiments, the closure members 38, 40, 44 are adhered, for example, by an adhesive 62, to the pouch 10. In embodiments, the members 38, 40, 44 need not be fully adhered to the pouch 10. As seen in FIG. 5, in the direction of the length of the pouch 10, that is in the direction along the centerline $A_{28}$ of the outlet 28, the entirety of the closure members 38, 40, 44 need not be fully adhered to the pouch 10. Portions, as indicated at 64, of the first and second members 38, 40 nearer to one another can be unadhered to the pouch 10, or the members 38, 40 can be fully adhered to the pouch 10. A portion, as indicated at 66, of the third member 44 nearer to the enlarged head portion 48 can be unadhered to the pouch 10. This will allow for elastic deformation, e.g., stretching, of the pouch 10 films between the first and second members 38, 40 (as at fold line 58) when effecting the first fold 58 and stretching, of the pouch 10 films beyond the second and third members 40, 44 (as at fold line 60) when effecting the second fold 60.

Figure 6A:
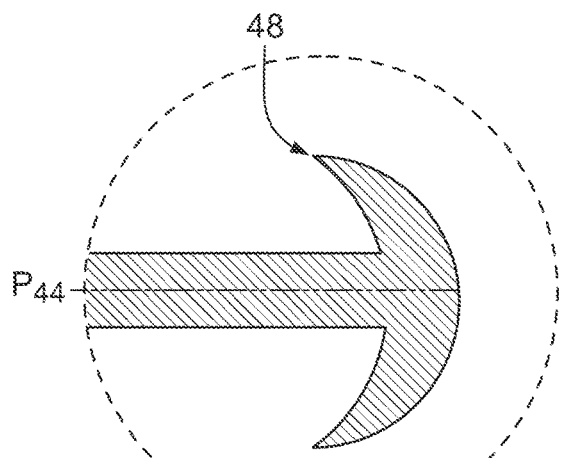
FIGS. 6A-6C illustrate various embodiments of enlarged head portions or wiper seals.
Figure 6B:
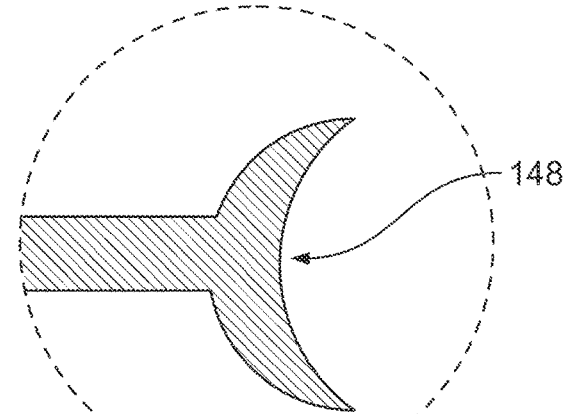
Figure 6C:
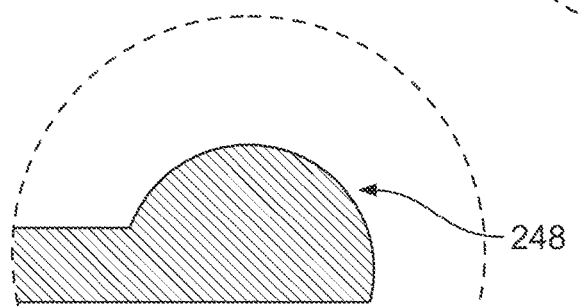

Referring now to FIGS. 6A-6C, there are shown embodiments of the enlarged head portion of the wiper seal 46. As noted above, in an embodiment, as seen in FIG. 6A, the head portion 48 has a rounded arrowhead shape or a closed parenthesis shape. In an alternate embodiment, as seen in FIG. 6B, the enlarged head portion 148 can have an opposite shape, that is an inverted arrowhead or open parenthesis shape. Still another embodiment is shown in FIG. 6C in which the enlarged head portion 248 has a semicircular shape formed on one side of the closure member 244. It will thus be appreciated that the enlarged head portion 48, 148, 248 wiper seal 46 can be symmetrical relative to the plane ($P_{44}$ as seen in FIG. 6A) of the closure member 44, or it can be asymmetrical relative to the plane of the member.

Figure 8A:
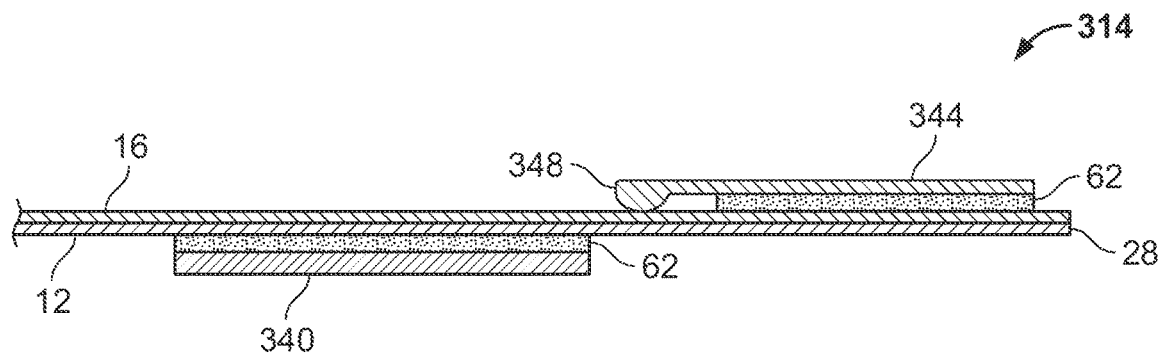
FIGS. 8A-8C are sectional views of the pouch including a closure system according to another embodiment illustrating the folding of the closure system.
Figure 8B:
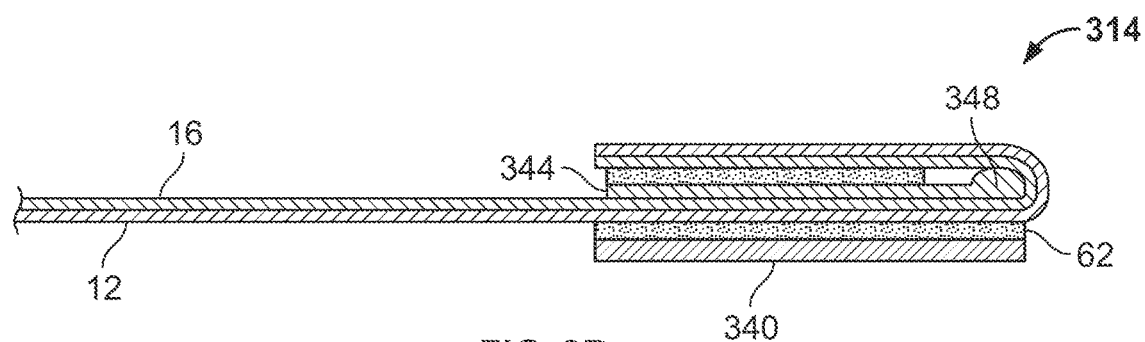
Figure 8C:
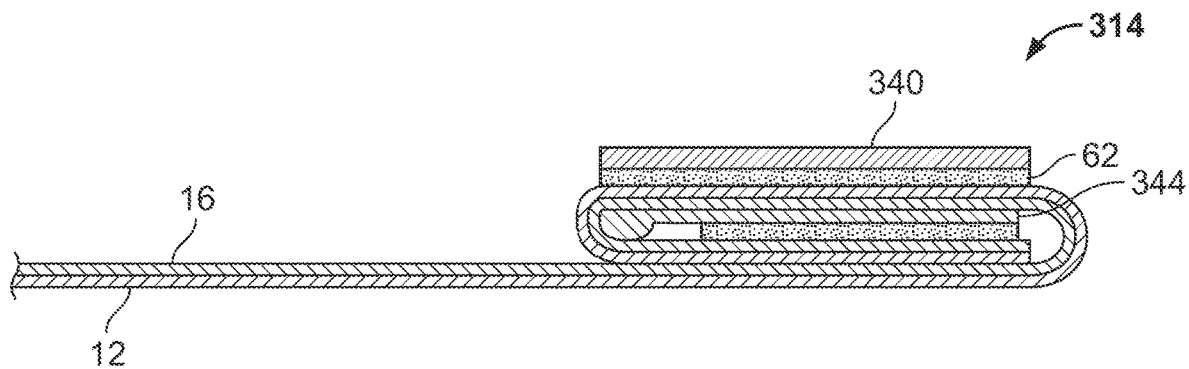

Referring now to FIGS. 8A-8C there is shown a closure system 314 according to another embodiment. The closure system 314 may include a body side closure member 340 attached to the body side wall 12 via an adhesive 62 and a non-body side closure member 344 attached to the non-body side wall 16 via an adhesive 62. In this embodiment, the non-body side closure member 344 may be arranged proximal to the discharge outlet 28 and the body side closure member 340 may be arranged spaced away from the discharge outlet 28, such that the body side closure member 340 does not overlie the non-body side closure member 344. The non-body side closure member 344 may include an enlarged portion 348 at the upstream (i.e., away or distal from the discharge outlet 28). The enlarged portion 348 may have various shapes, such as those shown in FIGS. 6A-6C. In the embodiment of FIGS. 8A-8C, the enlarged portion 348 may have a semicircular shape formed on the non-body side wall 16 facing surface of the closure member 344.

The folding of the pouch neck portion 26 including the closure system 314 may be similar to the folding of the pouch neck portion 26 including the closure system 14 shown in FIGS. 4A-4C. In the embodiment of FIGS. 8A-8C, the non-body side closure member 344 is folded onto the body side closure member 340 at a first fold as shown in FIG. 8B, wherein the body side wall 12 and the non-body side wall 16 are folded over the enlarged portion 348 of the non-body side closure member 344. Subsequently, the body side closure member 340 and the non-body side closure member 344 are folded together onto the non-body side wall 16 for a second fold as shown in FIG. 8C.

It will be appreciated that unlike known closure systems, the present closure system 14, 314 is not as dependent upon locational tolerances between the first and second (body side) closure members 38, 40, 340 and the third (non-body side) closure member 44, 344. That is, the alignment of the body side closure members 38, 40, 340 and the non-body side closure member 44, 344 is not as critical as with prior known closure systems because the present closure system 14, 314 uses the fold between the closure members in conjunction with the wiper seal 46 formed by the enlarged head portion 48, 148, 248, 348.

It will be appreciated, although not shown in FIGS. 1-5 and 8A-8C as it is well known in the art, the ostomy pouch closure system 14, 314 also includes a fastening system for securing the pouch neck portion 26 in a folded up and closed position, for example, after the second fold as shown in FIG.

Figure 7:
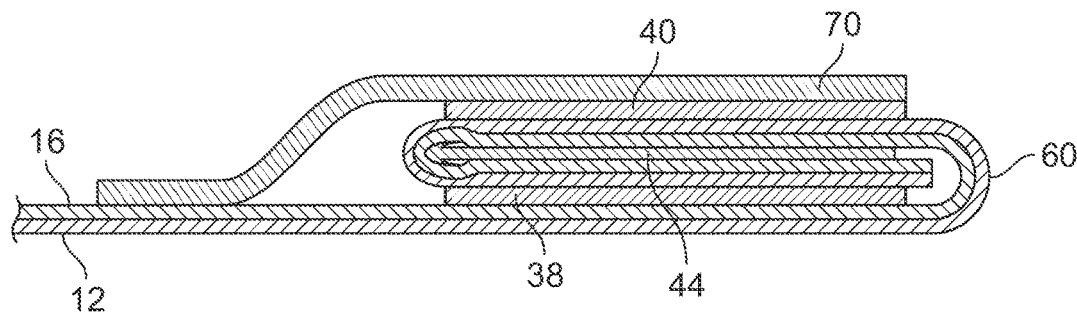
FIG. 7 is a sectional view of the pouch in the closed state of FIG. 4C secured via a two-part fastening system according to an embodiment.

4C or 8C. In some embodiments, the ostomy pouch closure system 14, 314 may include a two-part fastening system comprising first and second fastener strips, such as hook and loop fasteners. In an embodiment, the closure system 14, 314 may include a flap 70 attached to the non-body side wall 16 at upstream of the non-body side closure member 44, wherein the flap includes a first fastener strip and the second (body side) closure member 40, 340 includes a second fastener strip configured to engage with the first fastener strip to secure the folded neck portion in a closed position as shown in FIG. 7. Alternatively, the second (body side) closure member 40, 340 may be replaced with a second fastener strip. In another embodiment, the second fastener strip may be attached to the body side wall 12 adjacent the second (body side) closure member 40, 340, wherein the pouch neck portion 26 may be configured to be folded three times (a third fold after the second fold shown in FIG. 4C or 8C) and secured in a closed position by engaging the first fastener strip provided on the flap 70 with the second fastener strip.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular. In additions, various features described with respect to any of the embodiments above may be used together, implemented in, or replace features in any of the other embodiments described above.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. A drainable ostomy appliance, comprising:
side walls of flexible sheet material sealed to one another along a portion of their respective peripheries to define a collection cavity, the side walls being a body side wall and a non-body side wall, the side walls defining a downwardly extending neck portion terminating in a discharge outlet at which the side walls are not sealed to one another, the discharge outlet being closed by folding the neck portion upwardly and opened by unfolding the neck portion downwardly for draining the contents from the cavity;
an inlet in the body side wall; and
a closure system comprising:
a first portion of the closure system on the body side wall and a second portion of the closure system on the non-body side wall, wherein the first portion of the closure system comprises at least one body side closure member and the second portion of the closure system comprises at least one non-body side closure member including an enlarged head portion on an end thereof, and
a fastening system,
wherein in an open state, the neck portion is unfolded and in a closed state, the neck portion is folded upwardly at least two times and secured in the closed state using the fastening system, wherein the side walls of the neck portion are folded around the enlarged head portion of the at least one non-body side closure member at a first fold.

2. The ostomy appliance of claim 1, wherein the at least one body side closure member includes a first closure member and a second closure member, the first closure member being proximal the discharge outlet and the second closure member being distal of the discharge outlet, the first and second closure members defining a gap therebetween, wherein the at least one non-body side closure member includes a third closure member, the third closure member having the enlarged head portion forming a wipe seal on an end thereof proximal the discharge outlet, and wherein in the closed state, the first closure member is folded onto the third closure member with an edge of the first member engaging the enlarged head portion through the side walls, and the first, second and third closure members are folded over onto the non-body side wall at a tight fold to seal the discharge outlet.

3. The ostomy appliance of claim 2, wherein the first and second closure members have preferential fold lines formed therein.

4. The ostomy appliance of claim 3, wherein the preferential fold lines are slits formed into a portion of the first and second closure members.

5. The ostomy appliance of claim 2, wherein the third closure member is formed of a material that is softer than a material from which the first and/or second closure members are formed.

6. The ostomy appliance of claim 1, wherein the at least one non-body side closure member includes a third closure member arranged proximal the discharge outlet and having the enlarged head portion on an end thereof distal of the discharge outlet, wherein the at least one body side closure member includes a first closure member arranged spaced away from the discharge outlet, and wherein in the closed state, the third closure member is folded onto the first closure member at the first fold and the first and third closure members are folded over onto the non-body side wall at a second fold.

7. The ostomy appliance of claim 1, wherein each of the at least one body side closure member and the at least one non-body side closure member is formed from a stiff, flexible, spring-like material.

8. The ostomy appliance of claim 7, wherein the material is a polymeric material.

9. The ostomy appliance of claim 8, wherein the polymeric material is polyethylene or ethylene vinyl acetate.

10. The ostomy appliance of claim 1, wherein the enlarged head portion has a rounded arrowhead shape.

11. The ostomy appliance of claim 1, wherein the enlarged head portion has an inverted, rounded arrowhead shape.

12. The ostomy appliance of claim 1, wherein the enlarged head portion is formed as a semicircular projection extending from a surface of the at least one non-body side closure member.

13. The ostomy appliance of claim 12, wherein the semicircular projection extends towards the non-body side wall.

14. The ostomy appliance of claim 1, wherein each of the at least one body side closure member is mounted to the body side wall such that a portion of each of the at least one body side closure member is adhered to the body side wall and another portion of each of the at least one body side closure member is not adhered to the body side wall.

15. The ostomy appliance of claim 14, wherein the at least one body side closure member includes first and second closure members, wherein the portion of each of the first and second closure members not adhered to the body side wall are proximal one another.

16. The ostomy appliance of claim 1, wherein each of the at least one non-body side closure member is mounted to the non-body side wall such that a portion of each of the at least one non-body side closure member is adhered to the non-body side wall and another portion of each of the at least one non-body side closure member is not adhered to the non-body side wall.

17. The ostomy appliance of claim 16, wherein the at least one non-body side closure member includes a third closure member, and the portion of the third closure member not adhered to the non-body side wall is proximal the enlarged head portion.

18. The ostomy appliance of claim 1, further including a two-piece coupling for securing to a user's body.

* * * * *